US012678245B2

(12) United States Patent
Zhou et al.

(10) Patent No.: US 12,678,245 B2
(45) Date of Patent: *Jul. 14, 2026

(54) INVERSE KINEMATICS OF A SURGICAL ROBOT FOR TELEOPERATION WITH HARDWARE CONSTRAINTS

(71) Applicant: Verb Surgical Inc., Santa Clara, CA (US)

(72) Inventors: Renbin Zhou, Santa Clara, CA (US); Haoran Yu, Santa Clara, CA (US); Seungkook Yun, Santa Clara, CA (US); Ellen Klingbeil, Santa Clara, CA (US); Apoorv Shrivastava, Santa Clara, CA (US)

(73) Assignee: Auris Health, Inc., Santa Clara, CA (US)

( * ) Notice: Subject to any disclaimer, the term of this patent is extended or adjusted under 35 U.S.C. 154(b) by 72 days.

This patent is subject to a terminal disclaimer.

(21) Appl. No.: 18/655,664

(22) Filed: May 6, 2024

(65) Prior Publication Data

US 2024/0285361 A1 Aug. 29, 2024

Related U.S. Application Data

(63) Continuation of application No. 16/896,404, filed on Jun. 9, 2020, now Pat. No. 12,004,829.

(51) Int. Cl.
*A61B 34/35* (2016.01)
*A61B 34/37* (2016.01)
(Continued)

(52) U.S. Cl.
CPC .............. *A61B 34/35* (2016.02); *A61B 34/37* (2016.02); *B25J 9/02* (2013.01); *B25J 9/101* (2013.01);
(Continued)

(58) Field of Classification Search
None
See application file for complete search history.

(56) References Cited

U.S. PATENT DOCUMENTS

| 1,513,535 | A | 10/1924 | Crumb |
| 5,019,968 | A | 5/1991 | Wang et al. |
| | | (Continued) | |

FOREIGN PATENT DOCUMENTS

| CN | 105101903 A | 11/2015 |
| CN | 106264732 A | 1/2017 |
| | (Continued) | |

OTHER PUBLICATIONS

International Search Report and the Written Opinion for International Patent Application PCT/US2020/038098 mailed Mar. 8, 2021.

(Continued)

*Primary Examiner* — Jason Holloway
*Assistant Examiner* — Bryant Tang
(74) *Attorney, Agent, or Firm* — Lempia Summerfield Katz LLC

(57) ABSTRACT

Various approaches to solve for inverse kinematics may be used for teleoperation of a surgical robotic system. In one approach, an iterative solver solves for the linear component of motion independently from solving for the angular component of motion. One solver may be used to solve for both together. In another approach, all limits (e.g., position, velocity, and acceleration) are handled in one solution. Where a limit is reached, the limit is used as a bound in the intermediate solution, allowing solution even where a bound is reached. In another approach, a ratio of limits of position are used to create a slow-down region near the bounds to more naturally control motion. In yet another approach, the (Continued)

medical-based teleoperation uses a bounded Gauss-Siedel solver, such as with successive-over-relaxation.

12 Claims, 7 Drawing Sheets

(51) Int. Cl.
  *B25J 9/02* (2006.01)
  *B25J 9/10* (2006.01)
  *B25J 9/16* (2006.01)
(52) U.S. Cl.
  CPC ........... *B25J 9/1607* (2013.01); *B25J 9/1648* (2013.01); *B25J 9/1651* (2013.01)

(56) References Cited

U.S. PATENT DOCUMENTS

| | | |
|---|---|---|
| 8,293,066 B2 | 10/2012 | Bluck |
| 8,716,973 B1 | 5/2014 | Lammertse |
| 9,101,379 B2 | 8/2015 | Au et al. |
| 9,743,898 B2 | 8/2017 | Wendler |
| 10,074,151 B2 | 9/2018 | Eldar |
| 10,085,809 B2 | 10/2018 | Blumenkranz et al. |
| 10,657,817 B2 | 5/2020 | Schoenherr et al. |
| 10,952,801 B2 | 3/2021 | Miller |
| 2013/0090763 A1 | 4/2013 | Simaan et al. |
| 2014/0005678 A1 | 1/2014 | Shelton, IV et al. |
| 2015/0305701 A1 | 10/2015 | Wendler |
| 2017/0172676 A1 | 6/2017 | Itkowitz et al. |
| 2018/0085926 A1 | 3/2018 | Kogan |
| 2019/0299416 A1 | 10/2019 | Watanabe et al. |
| 2020/0281676 A1 | 9/2020 | Rohs et al. |
| 2020/0297442 A1 | 9/2020 | Adebar et al. |

FOREIGN PATENT DOCUMENTS

| | | |
|---|---|---|
| CN | 109640867 A | 4/2019 |
| ES | 2351177 T3 | 2/2011 |
| JP | 4894657 B2 | 3/2012 |
| JP | 2019177436 A | 10/2019 |
| KR | 20160132896 A | 11/2016 |
| KR | 20200052980 A | 5/2020 |
| WO | 2017151996 A1 | 9/2017 |
| WO | 2019094794 A2 | 5/2019 |

OTHER PUBLICATIONS

Saudi, Azali, and Jumat Sulaiman. "Half-Sweep Gauss-Seidel (HSGS) iterative method for robot path planning." The 3rd Int. Conf. on Informatics and Technology (Informatics09), Kuala Lumpur. 2009. pp. RDTI-35-RDTI-39.
Saudi, Azali, and Jumat Sulaiman. "Robot path planning using Laplacian Behaviour-Based Control via Half-Sweep Gauss-Seidel (LBBCHSGS) iterative method." International Journal of Applied Mathematics and Statistics 36.6 (2013): 68-76.
Notice of Preliminary Rejection for Korean Patent Appln. No. 10-2023-7000403 mailed Aug. 6, 2025.
Baksic, Paul, et al. "Robotic needle insertion in moving soft tissues using constraint-based inverse Finite Element simulation." 2020 IEEE International Conference on Robotics and Automation (ICRA). IEEE, 2020.pp. 1-9.
European Search Report for European App. No. 20939915.3 mailed Jun. 6, 2024.
Notification to Grant Patent for App. No. CN 202080101931.4 mailed Dec. 10, 2025, with English summary.

300    Receive User Movement Command during Teleoperation

310    Solve for Robot Motion with Iterative Solution

311    Include All Limits in One Solution

312    Use Bounding Ratio for Graded Motion

313    BGSR Solver

314    Clamp to Limit for Non-Optimal but Usable Solution

315    Decouple Linear and Angular Solutions

316    Solve for X DOF in X-N DOF Teleoperation

320    Move the Robotic Arm or End-Effector

J6 - SPHERICAL ROLL JOINT
J7 - SPHERICAL PITCH A JOINT
J8 - TOOL TRANSLATE JOINT
J9 - TOOL ROTATION JOINT
J10 - TOOL PROXIMAL WRIST JOINT
J11 - TOOL DISTAL WRIST JOINT

INVERSE KINEMATICS OF A SURGICAL ROBOT FOR TELEOPERATION WITH HARDWARE CONSTRAINTS

RELATED APPLICATION

This application is a continuation of U.S. application Ser. No. 16/896,404, filed Jun. 9, 2020, which is hereby incorporated by reference in its entirety.

BACKGROUND

The present embodiments relate to robotic systems for minimally-invasive surgery (MIS). MIS may be performed with robotic systems that include one or more robotic arms for manipulating surgical tools based on commands from a remote operator. A robotic arm may, for example, support at its distal end various surgical end effectors, including scalpels, imaging devices (e.g., endoscope), clamps, and scissors. Using the robotic system, the surgeon controls the robotic arms in teleoperation during MIS.

Teleoperation converts user commands to robotic arm and surgical tool joint commands as an inverse kinematic problem. The inverse kinematic problem may need to deal with different numbers of degrees of freedom (DOF), depending on the end effector being used. For example, a clamp has six degrees of freedom in teleoperation. After braking one or more joints once positioned for operation, six active joints, and corresponding six DOF, are provided by three joints on the surgical tool (e.g., rotation, pitch, and yaw), and three joints on the robotic arm (e.g., spherical rotate, spherical pitch, and tool translate). As another example, staplers have five DOF in teleoperation. Five active joints, and corresponding DOF, includes two joints on the instrument (e.g., rotation and articulate) and three joints on the robotic arm (e.g., spherical rotate, spherical pitch, and tool translate). In yet another example, an endoscope or ultrasound scalpel has four DOF in teleoperation. Four active joints, and corresponding DOF, include one joint on the instrument (e.g., rotation) and three joints on the robotic arm (e.g., spherical rotate, spherical pitch, and tool translate).

During teleoperation, the user inputs with six DOF, which commands are translated into joints motions, such that the instrument follows the user commands with controlled accuracy. To convert user commands to joint commands, an inverse kinematic function is solved. One example is given as:

$$\Delta_{common\ d\_i} = J_i \Delta \theta_i,$$

where $\Delta_{command\_i}$ is user command matrix (6×1) in task space at current time i, I is Jacobian matrix (6×n) at current time i, and $\Delta \theta_i$ is a joint motion matrix (n×1) at current time i. Due to physical constraints on the robotic arm and surgical tool (e.g., joint position limits, joint velocity limits, and joint acceleration limits), an exact solution may not be achievable when one or more of these constraints are violated by the solution.

SUMMARY

By way of introduction, the preferred embodiments described below include methods, systems, instructions, and computer readable media for teleoperation of a surgical robotic system. Various approaches to solve for inverse kinematics may be used. In one approach, an iterative solver solves for the linear component of motion independently from solving for the angular component of motion. One solver may be used to solve for both together. In another approach, all limits (e.g., position, velocity, and acceleration) are handled in one solution. Where a limit is reached, the limit is used as a bound in the intermediate solution, allowing solution even where a bound is reached. In another approach, a ratio of limits of position are used to create a slow-down region near the bounds to more naturally control motion. In yet another approach, the medical-based teleoperation uses a bounded Gauss-Siedel solver, such as with successive-over-relaxation. Any of these approaches may be used together or separately.

In a first aspect, a method is provided for teleoperation of a surgical robotic system. A user command to move a robotic arm or surgical tool of the robotic arm is received during the teleoperation. Linear motion of the move is solved in a first stage. Angular motion of the move is solved in a second stage separate from the first stage. The robotic arm or surgical tool of the robotic arm is moved based on the solutions for the linear motion and the angular motion.

In a second aspect, a method is provided for teleoperation of a surgical robotic system. A user command to move a robotic arm or surgical tool of the robotic arm is received during the teleoperation. The motion by the robotic arm or the surgical tool of the robotic arm is solved for with an iterative solution where the iterative solution includes solution considering all limits on the motion. The robotic arm or surgical tool of the robotic arm is moved based on the iterative solution.

In a third aspect, a surgical robotic system is provided for medical teleoperation. A surgical instrument connects to a robotic arm. A controller is configured to solve for motion of the robotic arm and/or surgical instrument during the medical teleoperation on a patient and in response to user input of a move command. The solution uses a bounded Gauss-Seidel solver with successive-over-relaxation.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

3

Figure 6:
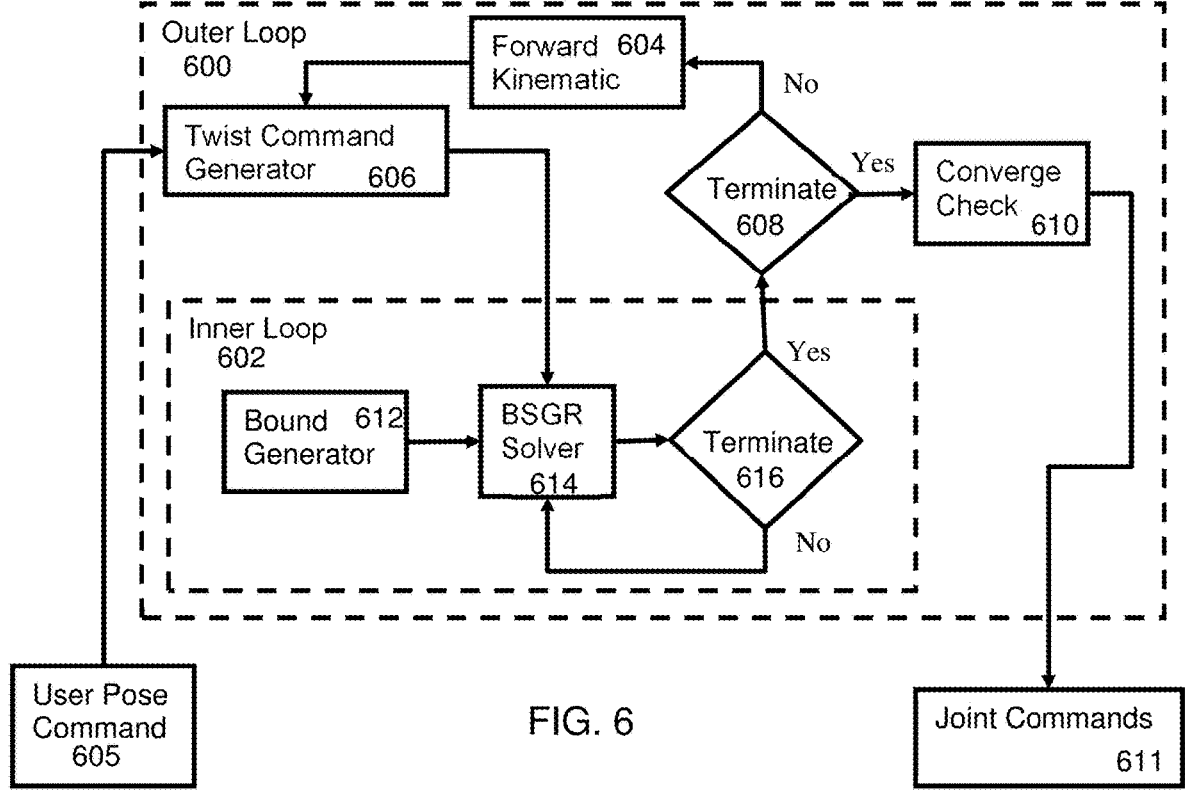
Figure 7:
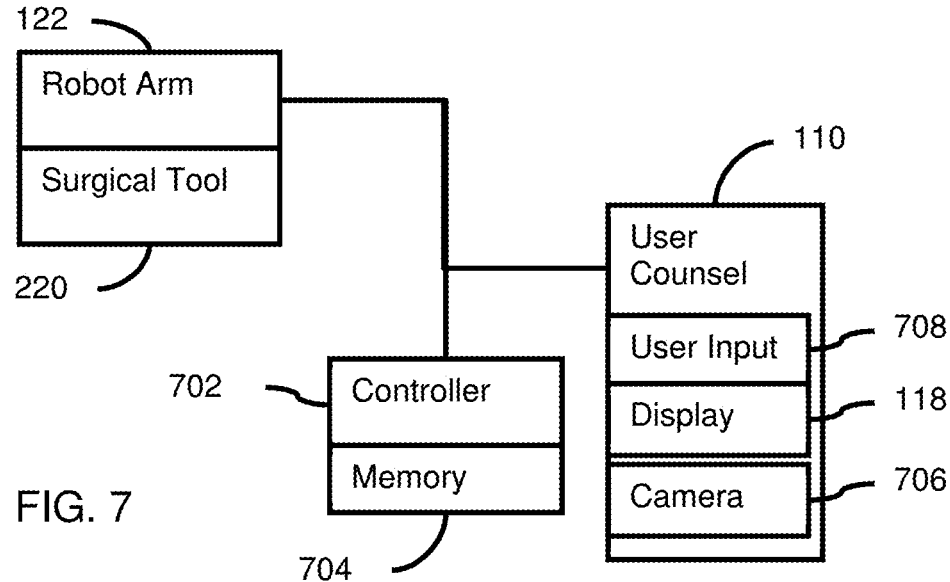

FIG. 6 is a flow chart diagram of one embodiment of nested control loops for iterative solution of inverse kinematics in teleoperation; and FIG. 7 is a block diagram of one embodiment of a surgical robotic system.

DETAILED DESCRIPTION OF THE DRAWINGS AND PRESENTLY PREFERRED EMBODIMENTS

Iterative inverse kinematics provide a unified framework to solve six, five, and four DOF problems. Joint position limits, joint velocity limits, and joint acceleration limits are handled in a single solution. The joint limits, velocity limits, and acceleration limits based on hardware are consolidated. Six, five, and four DOF inverse kinematics may use the iterative solution in a decoupled manner where linear motion and angular motion commands are solved independently. Where there is no limit violation, an exact solution (within tolerance) is provided. Where there is a limit violation, a solution, while sub-optimal, may still be provided. The value of the violated limit is used in the solution, clamping the position, velocity, and/or acceleration to the limit at least in an intermediate solution in the iterative inverse kinematics.

Figure 1:
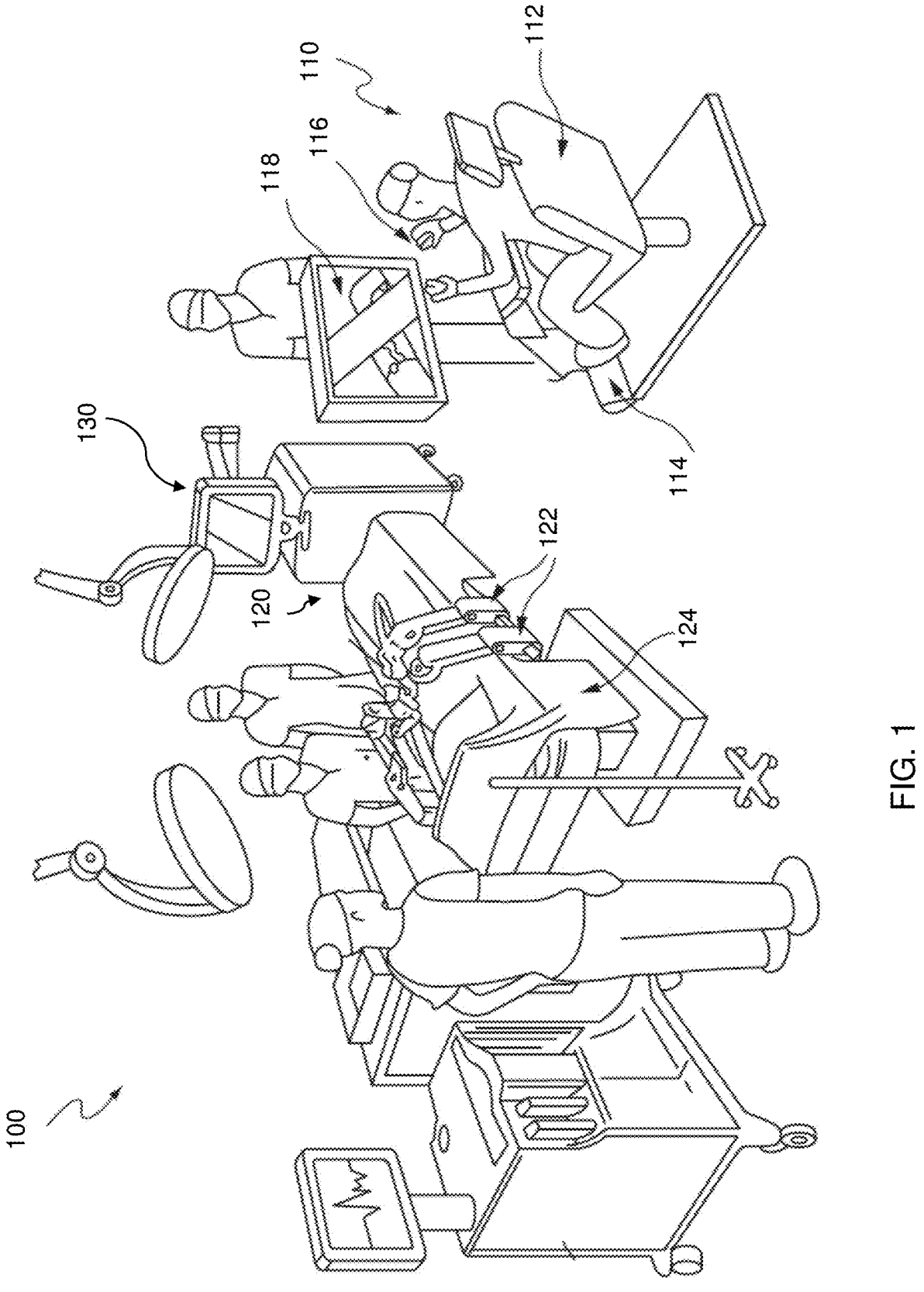
FIG. 1 is an illustration of one embodiment of an operating room environment with a surgical robotic system according to one embodiment.
Figure 2:
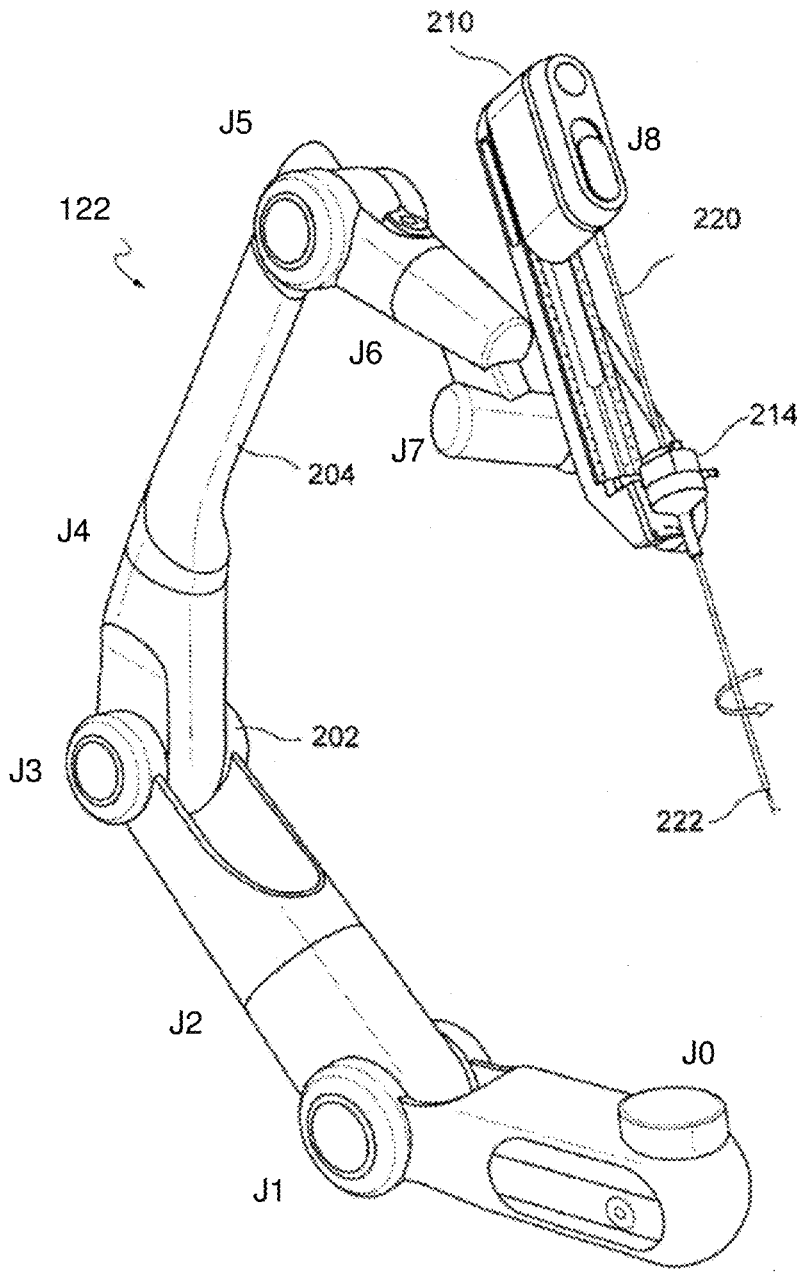
FIG. 2 illustrates an example surgical robot arm and surgical tool.

FIGS. 1 and 2 show an example surgical robotic system. The approaches for iterative inverse kinematic solution in teleoperation are discussed below in reference to this example system. Other surgical robotic systems and surgical robots or non-surgical robotic systems and robots may use the approaches.

FIGS. 3-6 are directed to iterative inverse kinematic solution in teleoperation. FIG. 7 is directed to a system for using an iterative inverse kinematic solver with a medical robotic system for teleoperation.

FIG. 1 is a diagram illustrating an example operating room environment with a surgical robotic system 100 for which commands from the user are converted into motion of the surgical robotic arms 122 with iterative inverse kinematics. The surgical robotic system 100 includes a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. Additional, different, or fewer components may be provided, such as combining the control tower 130 with the console 110 or surgical robot 120. The robotic arms 122 are shown as table-mounted, but in other configurations, the robotic arms 122 may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may include a seat 112, pedals 114, one or more handheld user interface devices (UIDs) 116, and an open display 118 configured to display, for example, a view of the surgical site inside a patient and graphic user interface. As shown in the exemplary user console 110, a surgeon sitting in the seat 112 and viewing the open display 118 may manipulate the pedals 114 and/or handheld user interface devices 116 to remotely and directly control the robotic arms 122 and/or surgical instruments mounted to the distal ends of the arms 122. The user inputs commands for the movement of the surgical arms 122 and/or end effectors. This user control determines position, the rate and change in rate of movement of the robotic arms 122. The rate and change in rate result in dynamic torque expected to be provided by the robotic arms 122. The surgeon sitting in the seat 112 may view and interact with the display 118 to input commands for movement in teleoperation of the robotic arms 122 and/or surgical instruments in the surgery.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery using teleoperation. The movements may be surgeon, patient, and/or situation specific, so may vary. Manual assistance may also be provided at the procedure table by sterile-gowned personnel, who may perform tasks including but not limited to, retracting tissues or performing manual repositioning or tool exchange involving one or more robotic arms 122. Some surgical tasks, such as retracting, suturing, or other tissue manipulation, may instead be performed by one or more robotic arms 122 (e.g., third or fourth arms). Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input commands from the user console 110 to robotic control commands and transmit the control commands to the surgical robot 120. The control tower 130 performs iterative inverse kinematics. The control tower 130 may also transmit status and feedback from the robot 120 back to the user console 110. The connections between the surgical robot 120, the user console 110, and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic health-care record system.

Prior to initiating surgery with the surgical robotic system, the surgical team can perform preoperative setup. During the preoperative setup, the main components of the surgical robotic system (e.g., table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms 122 from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 122 over the patient and attach each arm 122 to a corresponding sleeve. The surgical robotic system 100 has the capability to uniquely identify each tool (endoscope and surgical instruments) upon attachment and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery as teleoperation using the tools controlled by two master UIDs 116 and foot pedals 114. The system translates the surgeon's hand, wrist, and finger movements through the master UIDs 116 into precise real-time movements of the surgical tools. Therefore in direct teleoperation, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

FIG. 2 is a schematic diagram illustrating one exemplary design of a robotic arm, a tool drive, and a cannula loaded with a robotic surgical tool, in accordance with aspects of the subject technology. As shown in FIG. 2, the example surgical robotic arm 122 may include a plurality of links (e.g., a link 202) and a plurality of actuated joint modules (e.g., a joint 204, see also joints J1-8) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 122. The tool drive 210 may include a cannula 214 coupled to its end to receive and guide a surgical instrument or end effector 220 (e.g., endoscopes, staplers, scalpel, scissors, clamp, retractor, etc.). The surgical instrument (or "tool") 220 may include an end effector 222 at the distal end of the tool. The plurality of the joint modules of the robotic arm 122 can be actuated to position and orient the tool drive 210, which actuates the end effector 222 for robotic surgeries. The end effector 222 is at a tool shaft end. In other embodiments, the tool shaft end is a tip of a needle or other object.

In the example of FIG. 2, the joint J0 is a table pivot joint and resides under the surgical table top. Joint J0 is nominally held in place during surgery. Joints J1 to J5 form a setup or Cartesian arm and are nominally held in place during surgery, so do not contribute to motion during surgical teleoperation. Joints J6 and J7 form a spherical arm that may actively move during surgery or teleoperation. Joint J8 translates the tool 220, such as the end effector 222, as part of a tool driver. Joint J8 may actively move during surgery. Joints J6-8 actively position a tool shaft end (i.e., end effector 222) during surgery while maintaining an entry point into the patient at a fixed or stable location (i.e., remote center of motion) to avoid stress on the skin of the patient. During set-up, any of the joints J0-J8 may move. During surgery, the joints J6-8 may move subject to hardware or safety limitations on position, velocity, acceleration, and/or torque. The surgical tool 220 may include none, one, or more (e.g., three) joints, such as a joint for tool rotation plus any number of additional joints (e.g., wrists, rotation about a longitudinal axis, or other type of motion). Any number of degrees of freedom may be provided, such as the three degrees from the joints J6-8 and none, one, or more degrees from the surgical tool 220.

Figure 3:
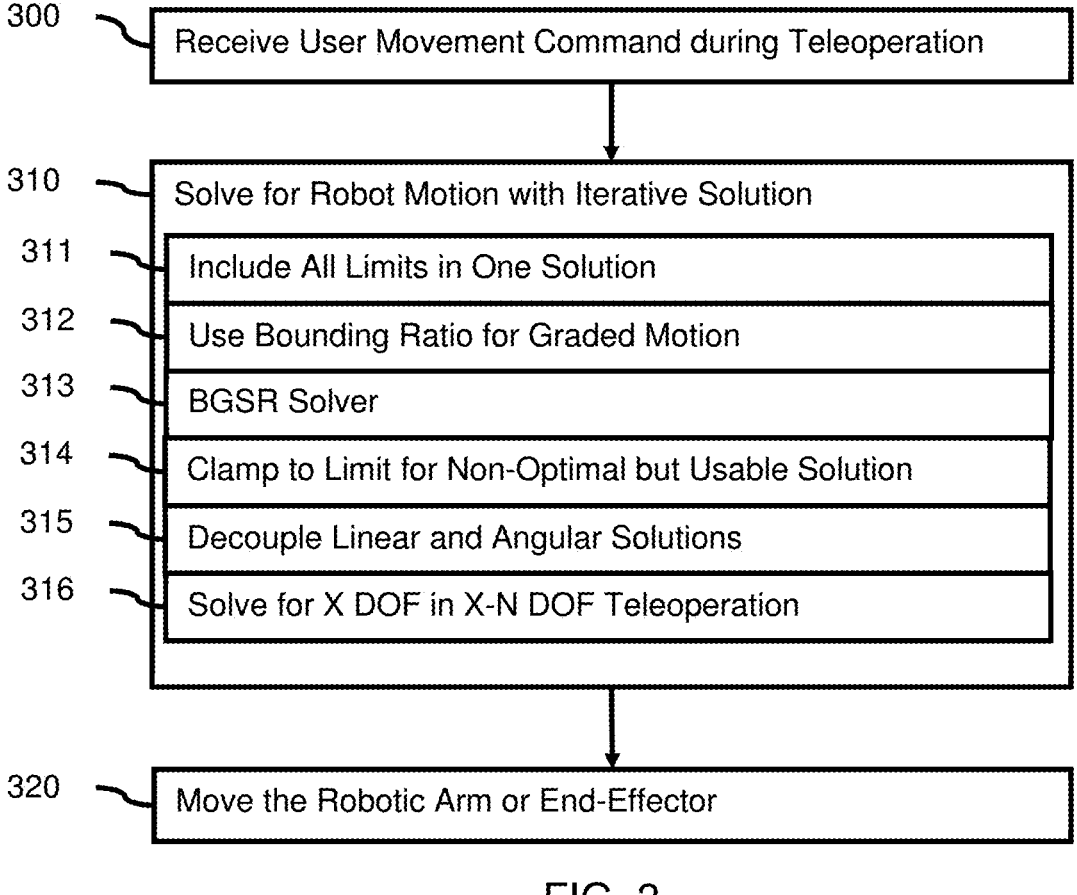
FIG. 3 is a flow chart diagram of one embodiment of a method for teleoperation of a surgical robotic system.

FIG. 3 is a flow chart diagram of one embodiment of a method for teleoperation of a surgical robotic system. Iterative inverse kinematics are used to convert user commands to a solution for movement of a robotic arm and surgical tool. Separate and independent linear and angular solutions, inclusion of all limits in one solution, bounding intermediate solutions to one or more limits when a limit is reached, using a ratio of position bounds to step down movement near a limit, and/or use of a bounded Gauss-Siedel solver in medical teleoperation may be used.

The method of FIG. 3 is implemented by a control processor, such as the control tower 130, computer, work-station, sever, or another processor. Any computer of the surgical robotic system 100 may be used. A user interface provides the movement commands from the user received in act 300. The robotic arm 122 and/or surgical tool 220 are moved using the instructions or control from the control processor in act 320. Other devices may perform and/or be used in any of the acts.

The acts are performed in the order shown or other orders. The various acts 311-316 that are part of the solving of act 310 may be performed in any order and/or simultaneously (e.g., as part of the same solution translating user commands to robotic arm and surgical tool movement).

Additional, different, or fewer acts may be used. For example, any of acts 311-316 may be performed alone in the solving of act 310. Any combination of two or more of any of acts 311-316 may be performed without others of the acts. In another example, acts for initially positioning the surgical tool 220 in the patient, planning surgery, and/or removing the surgical tool 220 from the patient may be provided.

In act 300, the control processor receives a user command to move a robotic arm 122 or surgical tool 220 of the robotic arm 122 during the teleoperation. The user input is received from the user console 110, such as the pedals 114 or user interface devices 116, via wireless or wired interface by the control processor. In other embodiments, the user commands are received by loading from memory or transmission over a computer network.

In preparation for teleoperation, the user sits down at the surgeon console 110. After positioning of the robot arm 122 for teleoperation, one or more joints are locked in place with a fixed remote center of motion (RCM) at the patient skin or incision entry point. For example, joints J0-J5 (see FIG. 2) are locked. The locking is by a brake and/or avoiding energizing the motors for the joints. These joints remain locked during teleoperation.

During teleoperation, the user enters commands to move the robotic arm 122 and/or surgical tool 220. The commands are for motion. Different commands may be provided for different movements. The commands may be for movement of the end effector 222. These commands may not be for movement of particular joints. The control processor is to convert the movement commands to controls of particular joints of the robotic arm 122 and/or surgical tool 220.

In one embodiment, user motion is tracked using a sensor. For example, the user holds a device, such as a pen or a UID 116. A magnetic position sensor and/or inertial measurement unit may be used to determine position and/or change in position of the pen or UID 116. As another example, the user holds a marker with a structure allowing for visual tracking, such as optical patterns or structures on one or more parts of the marker. A stereo camera and/or depth camera tracks the motion of the marker.

Figure 4:
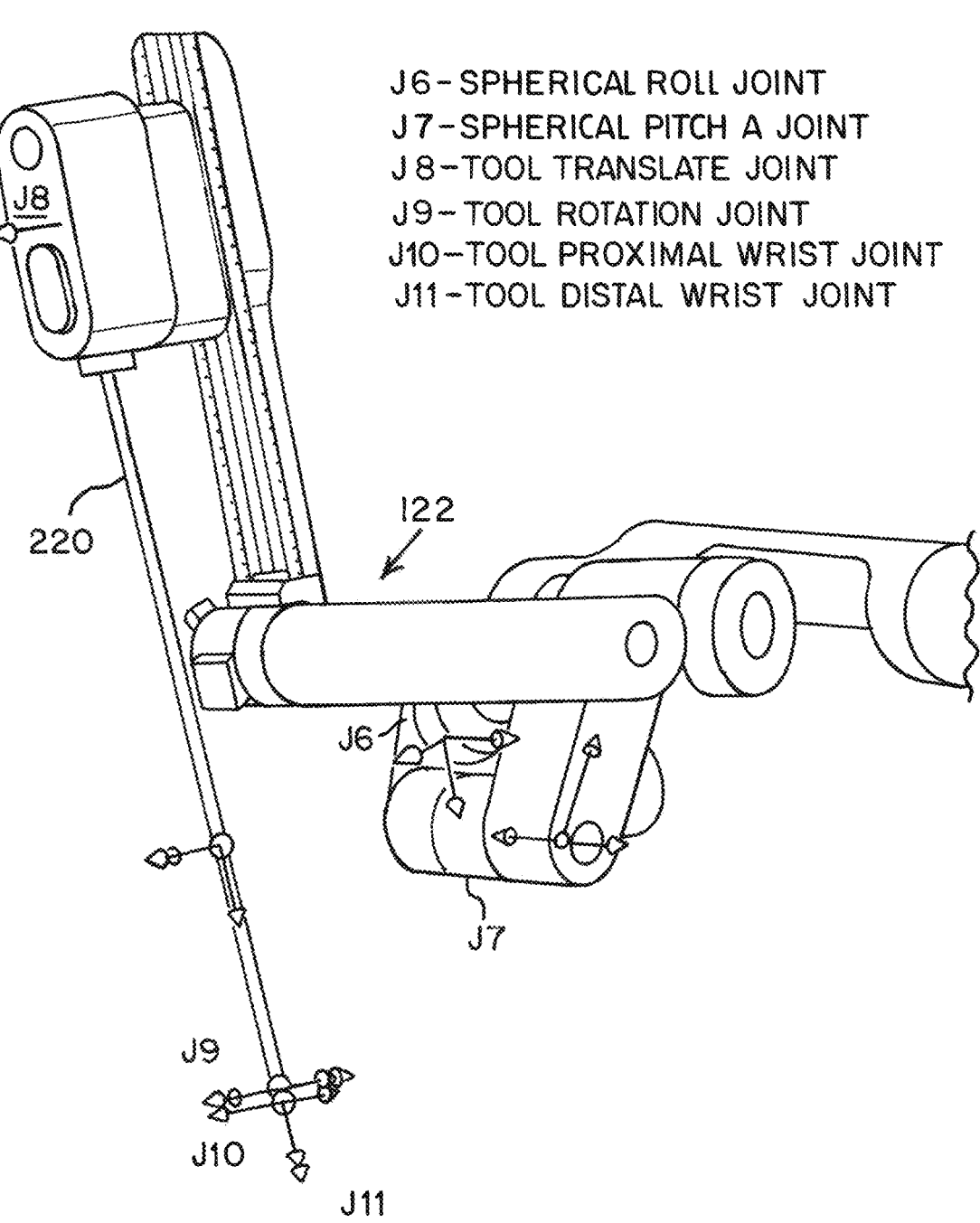
FIG. 4 shows an example robotic arm and surgical tool for six DOF.

The user commands may be for movement in any number of DOF. FIG. 4 shows part of the robotic arm 122 and the surgical tool 220 providing six DOF. The six DOF correspond to movement of six active joints during teleoperation. The active joints include three joints on the surgical tool 220—rotation at joint J9, pitch at wrist joint J10, and yaw at wrist joint J11. The active joints include three joints on the robotic arm 122—spherical rotation joint J6, spherical pitch joint J7, and tool translation joint J8. Other joints providing the six degrees of freedom may be used.

Figure 5:
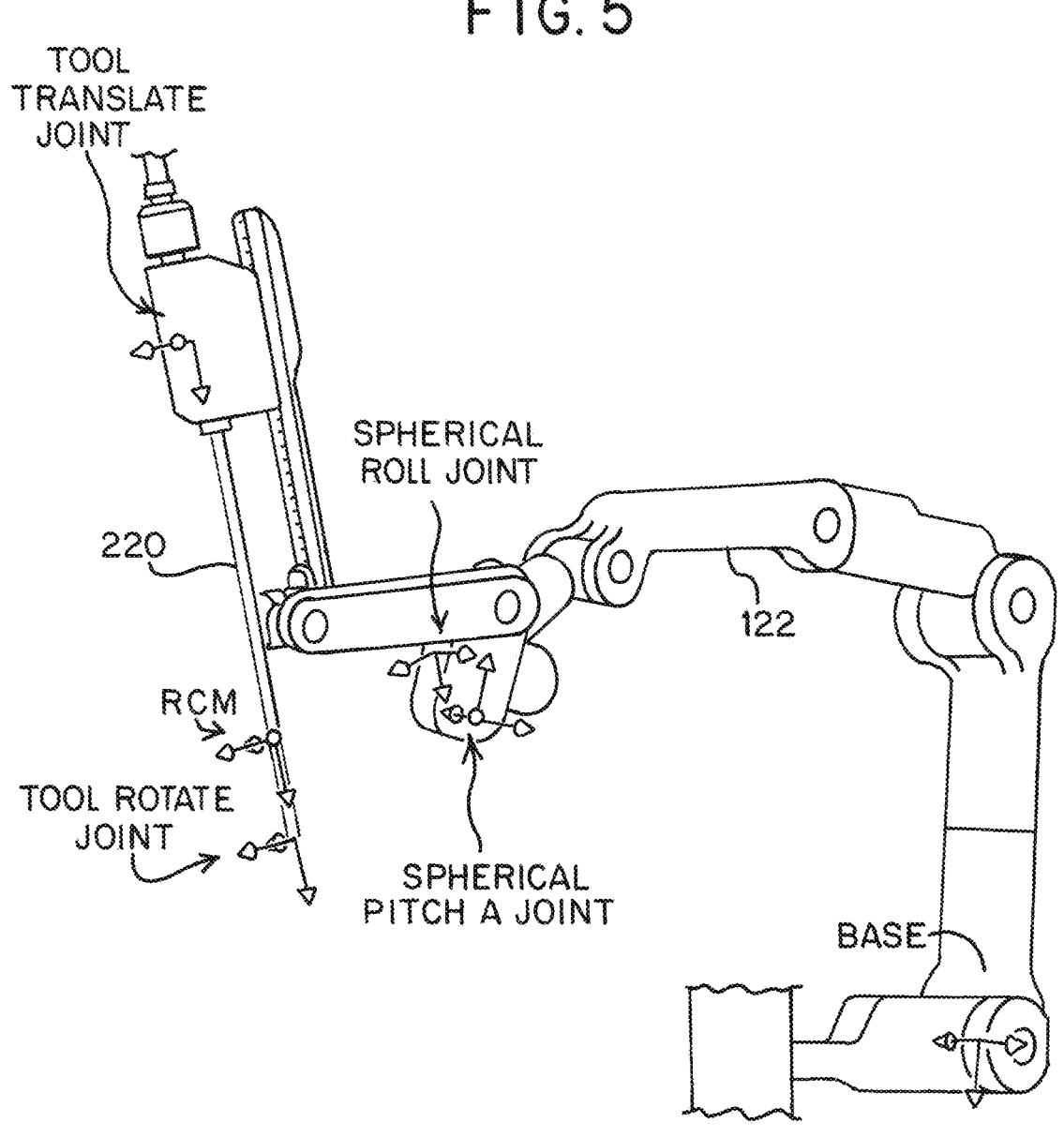
FIG. 5 shows an example robotic arm and surgical tool for four DOF.

The user commands may be for movement for fewer than six degrees of freedom. Five, four, or fewer active joints may be provided. FIG. 5 shows the robotic arm 122 and the surgical tool 220 providing four DOF, such as where the surgical tool 220 is an endoscope or ultrasound scalpel. The active joints include three joints on the robotic arm 122—spherical rotation joint J6, spherical pitch joint J7, and tool translation joint J8. The active joints include one joint on the surgical tool 220—rotation at joint J9. In an example of five DOF, the active joints include three joints on the robotic arm 122—spherical rotation joint J6, spherical pitch joint J7, and tool translation joint J8—and two actives joints on the surgical tool—rotation at joint J9 and articulation as another joint). Other active joint arrangements may be used, such as providing two or fewer DOF on the robotic arm during teleoperation.

In act 310, the control processor translates the movement commands from the user to movement of the joints. The control processor solves for motion by the robotic arm or the surgical tool of the robotic arm with an iterative solution. An iterative inverse kinematic solution is found.

Any control process may be used. The control process may be input of the user commands, iterative solution using inverse kinematics with a given termination check for the iterations, and output of a final result of joint commands. The iterative inverse kinematics uses one or more of: separate and independent linear and angular solutions, inclusion of all limits in one solution, bounding intermediate solutions to one or more limits when a limit is reached, using a ratio of position bounds to step down movement near a limit, and/or use of a bounded Gauss-Siedel solver in medical teleoperation.

FIG. 6 shows one embodiment of a nested loop control process. The outer control loop 600 is a main iterative inverse kinematic loop, and the inner control loop 602 is the iterative solver loop. An outer control loop 600 includes an inner control loop 602. The outer control loop 600 also includes a forward kinematic determination 604 of a position of the surgical tool 220, a twist command generation 606 of the move from the user command and the position of the surgical tool, a termination check 608, and a convergence check 610. The user pose command or the move 605 is input to the outer control loop. The twist command 606 is input to the solver 614 and the final solution is output to the termination check 608. The forward kinematic 604 computes the end effector 222 pose (i.e., position and orientation). This pose is input to the twist command generator 606. The twist command generator 606 computes the twist motion from the current end effector 222 pose to the pose command 605. Twist is a six DOF command (e.g., three DOF linear or translation and three DOF angular). For better convergence, linear twist is linearly interpolated with a step size ratio, and angular twist is interpolated with spherical linear interpolation(SLERP). Other interpolations may be used.

The termination check 608 of the outer control loop 600 checks for completion of joint commands 611 to be output to the robotic arm 122 and surgical tool 220. If not satisfied, the outer control loop 600 iterates through the forward kinematic determination 604, twist command generation 606, and the inner control loop 602. The termination check 608 for the outer control loop 600 uses one or more criteria. For example, three termination checks are performed where any one terminates the outer loop 600. The checks may include: (1) the commanded pose and current pose are compared for convergence check 610, (2) a maximum number of steps or iterations is reached, and (3) a timer expires. The convergence check 610 determines any error between computed pose command and the input pose command 605. The error is to be below a threshold level (i.e., the computed pose output by the solution from the solver 614 matches the input pose command 605 within a tolerance).

The various approaches to solving, including separate and independent linear and angular solutions, inclusion of all limits in each solution, bounding intermediate solutions to one or more limits when a limit is reached, using a ratio of position bounds to step down movement near a limit, and/or use of a bounded Gauss-Siedel solver in medical teleoperation, are discussed below in the context of the inner control loop 602 or herein in the nested control process of FIG. 6. Any of these approaches may be used in other control processes, such as with a single control loop for iterating through solutions.

The iterative inverse kinematic solver 614 is part of the inner control loop 602. The inner control loop 602 also includes a bound generator 612 and a termination check 616. The inner control loop 602 iterates through solutions of the solver 614 until the termination check 616 is satisfied. The solver 614 optimizes the solution. Additional, different, or fewer process units or software modules may be provided in the control process.

In the inner control loop 602, the bound generator 612 sets bound limits. The limits are related to hardware, safety, and/or other teleoperation requirements to bound the position, velocity, acceleration, torque, and/or other characteristic of movement of the robotic arm 122 and/or surgical tool 220.

In one embodiment, all of the limits or limitations on the linear component of the movement, on the angular component of the movement, and/or on both the linear and angular components of the movement are included in one solution as represented by act 311 (see FIG. 3). This single solution is for all motion of the robotic arm 122 and the surgical tool 220, for all linear motion, or for all angular motion. For example, all limitations or bounds for linear motion are provided in one single solution for the linear motion, and all limitations or bounds for angular motion are provided in one single solution for the angular motion. In iteratively solving for the translation of the user move command of the end effector 222 to the joint motions, all limitations are considered or dealt with in the solution. All the limitations are of the limitations being used, such as all of position, velocity and acceleration and not torque where torque is not used to limit motion. In alternative embodiments, different solving and solutions are provided for different sub-sets of the limitations being considered.

In one embodiment, the limits include positive and negative limits for each of position, velocity, and acceleration bounds. Positive and negative limits may be provided for torque bounds. The magnitude of the positive and negative limits may the equal or unequal. The limits are provided for each active joint and may be the same or different for different joints.

There are two joint position limits ($\theta_{min}$, $\theta_{max}$) for each active joint. A position limit ratio may be used to define a region of slow down to approach any of the position limits for any of the active joints in act 312 (see FIG. 3). In order to slow down the motion when approaching the limits, two additional limits ($\theta_{min}$, $\theta_{max}$), which form buffer zones by the position limit, are defined, such that, $$\theta_{max\_} = \theta_{max} - \theta_{offset} \tag{eq1}$$

$$\theta_{min\_} = \theta_{min} + \theta_{offset}$$

$$\theta_{offset})0$$

The offset may be any value, such as 5 mm.

These additional limits are used to determine a joint position bound ratio. Two joint position bound ratios, r, are calculated for each joint, one for each limit:

$$r_{\theta\_max} = 1.0, \text{ and } r_{\theta\_min} = -1.0, \text{ when } \theta_{min\_} < \theta < \theta_{max\_} \tag{eq2}$$

$$r_{\theta\_max} = (\theta - \theta_{max})/\theta_{offset}, \text{ when } \theta_{max\_} \le \theta \le \theta_{max}, \text{ or}$$

$$r_{\theta\_min} = (\theta - \theta_{min})/\theta_{offset}, \text{ when } \theta_{min} \le \theta \le \theta_{min\_}$$

From these two ratios, two joint motion bounds are calculated:

$$\Delta\theta_{max_\theta} = r_{\theta\_max} * (\theta_{max} - \theta), \text{ when } \theta_{max\_} \le \theta \le \theta_{max}, \text{ or,} \tag{eq3}$$

$$\Delta\theta_{min_\theta} = r_{\theta\_min} * (\theta_{min} - \theta), \text{ when } \theta_{min} \le \theta \le \theta_{min\_}$$

$[\Delta\theta_{min\theta}, \Delta\theta_{max\theta}]$, based on the position limit ratios, are used as a motion position bound due to joint limit constraints. The position bounds define a slow down region for velocity and acceleration slowing. Other ratios for the slow down and/or position limits or bounds may be used.

For each joint, there is a configurable maximum velocity limit $\omega_{max}$, such that joint velocity $\omega$ is inside range $[-\omega_{max}, \omega_{max}]$. Using the joint ratios from equation 2, the motion bounds due to joint velocity constraints are determined as:

$$\Delta\theta_{min_\omega} = r_{\theta\_min} * \omega_{max} * dt \tag{eq4}$$

$$\Delta\theta_{max_\omega} = r_{\theta\_max} * \omega_{max} * dt$$

$[\Delta\theta_{min}, \Delta\theta_{max}]$ are used as the motion bound due to joint velocity constraints.

For each joint, there is configurable maximum acceleration limit $\alpha_{max}$, such that joint acceleration is inside the range $[-\alpha_{max}, \alpha_{max}]$, when joint position is inside $[\theta_{min}, \theta_{max}]$ Using the joint ratios from equation 2, the motion bounds due to joint acceleration constraints are determined as:

$$\Delta\theta_{min_\alpha} = r_{\theta\_min} * (\omega_{prev} - 0.5 * a_{max} * dt) * dt \tag{eq5}$$

$$\Delta\theta_{max_\alpha} = r_{\theta\_max} * (\omega_{prev} + 0.5 * \alpha_{max} * dt) * dt$$

$[\Delta\theta_{min_n}, \Delta\theta_{max_n}]$ are used as the motion bound due to the acceleration limit.

Joint torque limits may be integrated into this framework. There are two force (torque) limits—a slowdown force/torque limit (F_slowdown) where motion slows down when past this limit and a stop force/torque limit (F_stop) where motion stops when reaching this limit. The force ratio is calculated as:

$$\text{force\_ratio} = 1.0, \text{ when } F < \text{F\_slowdown}$$

$$\text{force\_ratio} = (F - \text{F\_slowdown})/(\text{F\_stop} - \text{F\_slowdown}),$$

$$\text{when } F >= \text{F\_slowdown}.$$

Other limits, calculation of limits, and/or ratios may be used. The ratio for stepping down the motion in terms of position, velocity, and/or acceleration may be applied to torque as well or may not be used for one or more (e.g., all) of the limits.

For consideration of all the limitations in one solution, the limits are combined. The combined bounds are formed from the joint position bounds, joint velocity bounds, and joint acceleration bounds where force or torque is not limited. One example combination is given by:

$$\Delta\theta_{min} = \max(\Delta\theta_{min\_\theta}, \Delta\theta_{min\_\omega}, \Delta\theta_{min\_\alpha}) \tag{eq6}$$

$$\Delta\theta_{max} = \min(\Delta\theta_{max\_\theta}, \Delta\theta_{max\_\omega}, \Delta\theta_{max\_\alpha})$$

$[\Delta\theta_{min}, \Delta\theta_{max}]$ is used as the final combined bounds generated by the bound generator 612 for input to the solver 614. These combined bounds may be stored in memory and looked up or generated as needed.

Where torque or force limits are included, the combined limits are scaled by the force ratio, given by:

$$[\Delta\theta_{min}, \Delta\theta_{max}]_{fr} = \text{force\_ratio} * [\Delta\theta_{min}, \Delta\theta_{max}],$$

where $[\Delta\theta_{min}, \Delta\theta_{max}]$ is computed from equation 6, and $[\Delta\theta_{min}, \Delta\theta_{max}]$, is the final bounds for the solver 614. Other approaches to include force or torque limits may be used. Other combinations of limits may be used.

The solver 614 receives the bounds, such as all the bounds to be used in one solution, and the motion command from the generator 606. The solver 614 determines the joint motion as an optimization or iterative fitting.

Any optimization may be used, such as linear programming or quadratic programming. In one embodiment shown as act 313 of FIG. 3, a bounded Gauss-Seidel solver is used. The bounded Gauss-Seidel solver may include successive-over-relaxation (bounded Gauss-Seidel solver with successive-over-relaxation (BGSR)) but may be provided without successive-over-relaxation. BGSR is an iterative solver, which has an additional feature to clamp intermediate solutions to a bound. The main iteration step of a generic BGSR solver can be shown as:

$$x_i^{k+1} = x_i^k + r/a_{ii}\left(b_i - \sum_{j=1}^{i-1} a_{ij}x_j^{k+1} - \sum_{j=i}^{n} a_{ij}x_j^k\right) \quad \text{(eq7)}$$

$$\text{if } x_i^{k+1} \geq x_{i\_max}, x_i^{k+1} = x_{i\_max}, \text{ and}$$

$$\text{if } x_i^{k+1} \leq x_{i\_min}, x_i^{k+1} = x_{i\_min}$$

where r is successive-over-relaxation (SOR) ratio and $1.0 < r < 2.0$. k is an iteration index, $x_i$ are variables to be solved, and $[a_{ij}]$ and $[b_i]$ are linear coefficients. BGSR is guaranteed to converge if $[a_{ij}]$ is a positive definite matrix. In this implementation, a transformation is made to the Jacobian matrix in order to meet this condition.

$$J^T J v_{joint} = J^T * v_{command} \quad \text{(eq8)}$$

where J is Jacobian matrix (6×n) for 6 DOF, $v_{joint}$ is joint velocities (n×1) to be solved as $x_i$ in equation 7, and $v_{command}$ is the command velocity (6×1). "Joint" designates the active joints, such as J6-11, in teleoperation.

BGSR provides intermediate and final solutions through iteration. Where one of the solutions calls for a position, velocity, acceleration, or other parameter past a limit, the value for the limit or bound is used in the solution in act 314 (see FIG. 3). This clamps the intermediate or final solution to the bound in the position, velocity, and/or acceleration. Such clamping may be provided in optimization using other solvers than BGSR. By clamping in one or more iterations, the solution may continue to find the joint motions as a final solution. The limit may be used in the final solution or replaced by a value within the limit based on optimization. The final solution is possible even where the limits clamp to the boundary.

The inner loop termination check 616 checks for one or more criteria to either terminate upon satisfaction of one of the criteria or to iterate where none of the criteria are met. In one example, three criteria are used to terminate the iteration of the inner control loop 602: (1)$|J^T v_{joint\_k} - J^{\tau*} v_{command}| \leq$ tolerance, (2) a number of iterations is greater than a maximum number of iterations, and (3) an error reduction in BGSR is too small (e.g., $1.0^{e-3*tolerance}$) between adjacent steps or iterations.

The solver 614 can be implemented as a one stage solver, which solves linear and angular motion together. In an alternative embodiment shown as act 315 (see FIG. 3), the linear and angular motions are solved separately. Two stages of solving are provided. For example, the control process of FIG. 6 is performed separately for each of the linear motion stage and the angular motion stage. As another example, the inner control loop 602 is performed separately as the linear motion stage and the angular motion stage, which outputs are then used together in the outer control loop 600. The linear motion and angular motion stages have iterative solutions independent of each other. The linear motion is solved before the angular motion, but the reverse order may be used.

The decoupling of the motion components uses BGSR or another solver to solve for the motion components independently. The two functions being solved may be represented as:

$$(J_{upper\_left\ 3\times3})^T * \Delta_{linear} = (J_{upper\_left\ 3\times3})^T * J_{upper\_left\ 3\times3} * \Delta\theta_{6\_7\_8} \quad \text{(eq12)}$$

$$(J_{lower\_right\ 3\times3})^T * \Delta_{angular} = (J_{lower\_right\ 3\times3})^T * J_{lower\_right\ 3\times3} * \Delta\theta_{9\_10\_11}$$

$$\Delta\theta_{i\_min} \leq \Delta\theta_i \leq \Delta\theta_{i\_max}$$

where 6, 7, and 8 are for the active joints of the robotic arm 122 and 9, 10, and 11 are the active joints of the surgical tool 220. The lower, upper, left, and right are in reference to the part of the Jacobian matrix for the corresponding joints.

By decoupling the linear and angular stages, linear motion and angular motion are solved independently. Any limit violation affects linear motion and angular motion independently due to the decoupling. A limit violation in linear motion may not occur in angular motion component. An accurate solution, meeting tolerance requirements, is provided when there is no limit violation. A sub-optimal solution, still meeting tolerance requirements, is provided even when there is limit violation due to the clamping to the boundary.

The solution solves for six DOF. The solver is applied directly where the joint commands 611 are commands for each of the six joints. Where the robotic arm 122 and surgical tool 220 have fewer DOF, zero padding may be used to still provide a solution in act 316 of FIG. 3. Zero is used in terms for the linear and/or angular motion missing from the six DOF. For five DOF surgical instruments, the linear or angular motion solver can be applied directly (e.g. 3 DOF for linear), and the Jacobian matrix for angular or linear motion has only has two DOF (e.g., 2 DOF for angular). The Jacobian matrix (for angular in the example below) is expanded to three DOF as represented by:

$$[\Delta_{angular\_}, 0.0] = [A_{2\times2}, 0.0_{2\times1}] * [\Delta\theta_{9\_10}, 1.0]$$

$$[0.0_{1\times2}, 1.0]$$

For four DOF instruments, the linear or angular motion solver can be applied directly, and the Jacobian matrix for angular or linear motion only has one DOF. The Jacobian matrix (for angular in the example below) is expanded to three DOF, as resented by:

$$[\Delta_{angular\_}, 0.0, 0.0] = [A_{1\times1}, 0.0, 0.0] * [\Delta\theta_9, 1.0, 1.0]$$

$$[0.0, 1.0, 0.0]$$

$$[0.0, 0.0, 1.0]$$

In act 320 of FIG. 3, the control processor causes movement of the robotic arm 122 and/or the surgical tool 220. The output movement commands 611 for the active joints during teleoperation cause the joints to change position at the velocity and/or acceleration. The results from the iterative inverse kinematics control the movement of the joints (e.g., joints J6-11). In the decoupled linear and angular solutions, the linear and angular motions control movement of the corresponding joints.

Even where a sub-optimal solution is provided, real-time control of the robot arm 122 and surgical tool 220 is provided. The iterative solution translates the user commands to robot movement.

FIG. 7 shows a block diagram of one embodiment of a surgical robotic system for medical teleoperation. The system performs the method of FIG. 3, the control process of FIG. 6, or another method. Any one or more (e.g., all) of the solution approaches of FIG. 3, acts 311-316 may be used. An iterative inverse kinematic solution is provided for control of a robot arm 122.

The surgical robot system includes one or more robot arms 122 with corresponding surgical instruments 220 or other types of instruments connected with the robot arms 122, a controller 702, and a memory 704. The user counsel 110 is represented or included as part of the surgical robot system. Additional, different, or fewer components may be provided. For example, the robot arm 122, surgical instrument 220, and/or user counsel 110 are not provided.

The robotic arms 122 each include one or more links and joints. The joints may be pitch or roll joints. A tool drive and cannula for receiving and guiding a surgical tool may be provided on each of the robotic arms 122. Different combinations of links and joints may define or form different parts of the robotic arms 122, such as different parts having different degrees or types of movement (e.g., translation and/or rotation). Any now known or later develop robotic arm 122 with motors, sensors, links, joints, controllers, surgical instruments, and/or other structure may be used.

One or more robotic arms are provided. For example, three or four robotic arms 122 are provided. The robotic arms 122 mount to a table, such as a base of an operating table. Alternatively, cart, floor, ceiling, or other mounts may be used. The robotic arms 122 include a cable or wireless transceiver for communication with the processor 206 or an intermediary (e.g., control tower 130).

The robotic surgical instruments 220 are one or more graspers, retractors, scalpels, endoscopes, staplers, scissors, or other surgical device for manipulating tissue of the patient. The tissue manipulation may be direct, such as cutting or grasping. The tissue manipulation may be indirect, such as an endoscope pressing or contacting tissue as guided to image or view an interior portion of the patient. Different or the same type of instruments 220 may be mounted to different ones of the robot arms 122. For example, two robot arms 122 may have graspers, a third robot arm 122 may have a scalpel, and a fourth robot arm 122 may have an endoscope.

The robotic surgical instruments 220 connect to the distal ends of the robot arms 122 but may connect at other locations. The connection provides a drive so that the tool may be operated, such as closing a grasper or scissors.

The user counsel 110 is a graphics user interface for interaction of the surgeon with the surgical robot system, such as with a processor for controlling the robotic arms 122. The user interface includes a user input 708 and a display 118. The user input 708 and/or the display 118 are provided at the user console 110 and/or control tower 130 but may be at other locations.

The user input 708 is a button, a keyboard, a rocker, a joy stick, a trackball, a voice recognition circuit, a mouse, a touch pad, a touch screen, sliders, switches, UID 116, foot pedal 114, combinations thereof, or any other input device for inputting to the surgical robot. The display 118 is a monitor, liquid crystal display (LCD), projector, plasma display, CRT, printer, or other now known or later developed device for outputting visual information. In an alternative embodiment, the display 118 is a head mounted display. The user input 708 may be a sensor or sensors for detecting eye movement and/or blinking. In yet other embodiments, the user input 708 is a microphone for voice-based input. A speaker for output of audio information may be provided instead of or in addition to the display 118.

The optional camera 706 is a digital camera for optical tracking of user motion, such as tracking during use of the UID 116 to control the robot arm 122. The camera 706 may be a stereo camera and/or depth camera in some embodiments. The camera 706 is positioned relative to a user and a target pattern or user counsel 110 for tracking human motion in tracing the target pattern or controlling the robot arm 122 with the user input 708.

The controller 702 is a controller that drives and/or models the robotic arms 122 and/or surgical instruments 220. The controller 702 is a general processor, central processing unit, control processor, graphics processor, graphics processing unit, digital signal processor, application specific integrated circuit, field programmable gate array, digital circuit, analog circuit, artificial intelligence processor, combinations thereof, or other now known or later developed device for translating user commands to joint commands for the robot arm 122 and/or surgical instrument 220. The controller 702 is a single device or multiple devices operating in serial, parallel, or separately. The controller 702 may be a main processor of a computer, such as a laptop, server, workstation, or desktop computer, or may be a processor for handling some tasks in a larger system. Based on hardware, software, firmware, or combinations thereof, the controller 702 is configured to implement instructions or perform acts.

The controller 702 is configured solve for motion of the robotic arm 122 and/or surgical instrument 220 during the medical teleoperation on a patient and in response to user input of a move command through the user counsel 110. The controller 702 is configured to implement a solver, such as BGSR. An iterative solution using a bounded Gauss-Seidel solver with successive-over-relaxation is provided. The solution includes all limits on position, velocity, and acceleration of the robotic arm and surgical instrument in the one solution. All the limits used in the translation are handled in the solver to determine one solution for inverse kinematics. The controller 702 may be configured to solve for linear and angular components where the solving and solution for the linear components is independent of the solution for the angular components. The solving handles limit violations without failing. For example, an intermediate solution of the bounded Gauss-Seidel solver sets a position, velocity, or acceleration to a bound of the robotic arm 122 and/or surgical instrument 220. The solver determines the joint motion without violating the bounds.

The controller 702 is configured to control the robot arm 122 and surgical tool 220. Based on the solution, one or more joints are moved in response to user commands. The iterative inverse kinematic solution controls the joints.

The memory 704 or another memory is a non-transitory computer readable storage medium storing data representing instructions executable by the programmed controller 702. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Instructions are provided for any of the acts discussed herein. The instructions are for sizing, such as for design and/or testing of a surgical robot. The instructions are for generating a relationship between velocity and acceleration, generating a synthetic trajectory, and/or generating a virtual trajectory.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A surgical robotic system for teleoperation, the surgical robotic system comprising:

a robotic arm;

a surgical instrument coupled to a distal end of the robotic arm; and a controller configured to:

(1) receive a user command to move the surgical tool, (2) solve iteratively for linear motion of the move, providing a solution for the linear motion without solving for angular motion, (3) solve iteratively for the angular motion of the move, providing a solution for the angular motion without solving for the linear motion, the solution for the angular motion being decoupled as a separate solution than the solution for the linear motion such that any limit violation affects the linear motion and angular motion independently due to the decoupling, and (4) control the robotic arm based on the solution for the angular motion and the solution for the linear motion.

2. The surgical robotic system of claim 1 wherein, when the user command is received, the robotic arm has one or more joints locked in place with a fixed remote center of motion at a patient entry point.

3. The surgical robotic system of claim 1, wherein the user command is for teleoperation for fewer than six degrees of freedom, and wherein an optimization for the solution for the linear motion and/or an optimization for the solution for the angular motion includes use of a Jacobian matrix for six degrees of freedom with zero terms for the linear and/or angular motion not in the fewer than six degrees of freedom.

4. The surgical robotic system of claim 1, wherein an optimization for the solution for the linear motion is performed with all limitations on a linear component of the move of the robotic arm being in the solution for the linear motion, and wherein an optimization for the solution for the angular motion is performed with all limitations on an angular component of the move of the robotic arm being in the solution for the angular motion.

5. The surgical robotic system of claim 4, wherein a first term in the optimization for the solution for the linear motion includes positive and negative position, velocity, and acceleration bounds as all the limitations, and wherein a second term in the optimization for the solution for angular motion includes positive and negative position, velocity, and acceleration bounds as all the limitations.

6. The surgical robotic system of claim 1 wherein a limit violation effects the linear motion and the angular motion independently due to the decoupling.

7. The surgical robotic system of claim 1 wherein a position, velocity, or acceleration limit is used as a result in the solution for the linear motion and/or the solution for the angular motion.

8. The surgical robotic system of claim 1, wherein an optimization for the solution for the linear motion and an optimization for the solution for the angular motion each comprises a first control loop nested in a second control loop, wherein the first control loop includes a bound generator operating with a solver and a termination check for iterative solving by the solver, wherein the second control loop includes a forward kinematic determination of a position of the surgical tool, a command generation of the move from the user command and the position of the surgical tool, the move provided to the second control loop, and a second termination check receiving termination from the first control loop.

9. The surgical robotic system of claim 1 wherein the controller is configured to define a region of slow down to approach a position limitation of a joint of the robotic arm with a position limit ratio.

10. The surgical robotic system of claim 1 wherein an optimization for the solution for the linear motion and/or for the solution for the angular motion comprises application of a bounded solver.

11. The surgical robotic system of claim 10 wherein the bounded solver comprises a bounded Gauss-Seidel solver with successive-over-relaxation.

12. The surgical robotic system of claim 10 wherein the bounded solver clamps an intermediate solution to a bound in position, velocity, or acceleration of the robotic arm.

\* \* \* \* \*